(12) United States Patent
Stenzler et al.

(10) Patent No.: US 8,231,606 B2
(45) Date of Patent: Jul. 31, 2012

(54) METHOD AND DEVICE FOR REMOVING FLUID MATERIAL FROM THE AIRWAY ABOVE AN ENDOTRACHEAL TUBE CUFF

(75) Inventors: Alex Stenzler, Long Beach, CA (US); David Matthew Young, Gurnee, IL (US)

(73) Assignee: CareFusion 207, Inc., San Diego, CA (US)

( * ) Notice: Subject to any disclaimer, the term of this patent is extended or adjusted under 35 U.S.C. 154(b) by 1174 days.

(21) Appl. No.: 12/048,575

(22) Filed: Mar. 14, 2008

(65) Prior Publication Data

US 2009/0229615 A1  Sep. 17, 2009

(51) Int. Cl.
 *A61M 1/00* (2006.01)

(52) U.S. Cl. .................. 604/540; 128/207.14

(58) Field of Classification Search ............ 604/264, 604/319, 540; 128/207.14, 207.15
See application file for complete search history.

(56) References Cited

U.S. PATENT DOCUMENTS

| 6,460,540 | B1  | 10/2002 | Klepper |             |
|-----------|-----|---------|---------|-------------|
| 7,089,942 | B1* | 8/2006  | Grey    | 128/207.14  |
| 2007/0225555 | A1* | 9/2007 | Stefanchik | 600/104 |

\* cited by examiner

*Primary Examiner* — Melanie Hand

(57) ABSTRACT

A minimally invasive tracheal fluid removal device and corresponding method of use for removing accumulated subglottic secretions in an intubated patient's endotracheal tube. The device may be configured as a dual-track or single-tube suction guidance system. This device presents a significant improvement over the art as it eliminates the need to reintubate the patient each time the suction mechanism is removed to be cleaned.

14 Claims, 9 Drawing Sheets

METHOD AND DEVICE FOR REMOVING FLUID MATERIAL FROM THE AIRWAY ABOVE AN ENDOTRACHEAL TUBE CUFF

CROSS-REFERENCE TO RELATED APPLICATIONS

This application incorporates by reference U.S. patent application Ser. No. 11/981,570, for "Method and Device to Prevent Ventilator Acquired Pneumonia Using Nitric Oxide," filed Oct. 30, 2007, and U.S. patent application Ser. No. 11/978,940 for "Method and Device to Prevent Ventilator Acquired Pneumonia Using Nitric Oxide," filed Oct. 29, 2007, the disclosures of which are hereby incorporated by reference in their entireties.

FIELD OF THE INVENTION

The present invention relates generally to the field of endotracheal intubation, and also to a suction device and accompanying method of operation directed to the removal of accumulated tracheal fluid.

BACKGROUND OF THE INVENTION

Endotracheal intubation is used to mechanically inflate a patient's lungs when the patient is unable to breathe on his or her own. Gases with elevated oxygen concentrations may be introduced through the tube to treat the patient's deoxygenized condition. Notwithstanding its life-giving benefits, intubation also sometimes presents some risk to the patient as an accumulation and pooling of oral secretions laden with microorganisms can seep into the lungs and lead to infection. In some cases, the patient may ultimately be at risk of developing ventilator-acquired or ventilator-assisted pneumonia (VAP).

When a patient is intubated, a balloon cuff on the endotracheal tube located within the trachea inflates to seal the lungs from the outside so that the pressure from the ventilator can be kept in the lungs. VAP is an iatrogenic complication associated with some patients who require ventilation for more than a few days. A major causative mechanism is bacterial contamination of the lung by micro-aspirations of secretions that accumulate over the balloon cuff of an endotracheal or tracheotomy tube. If there is any leak around the cuff, the contaminated secretions can seep into the lungs and cause VAP.

Aspiration of the subglottic secretions has been shown to reduce the incidence of early VAP in intubated, ventilator-assisted patients. Rello, J. et al., *Pneumonia in intubated patients: role of respiratory airway care*, Am. J. Respir. Crit. Care Med. 154:111 (1996); Valles, J., et al., *Continuous aspiration of subglottic secretions in preventing ventilator assisted pneumonia*, Ann Intern. Med. 122:179 (1995).

The Hi-Lo Evac® Endotracheal tube with a secondary Evacuation Lumen, manufactured by Mallinckrodt, aims to provide one method for reducing VAP. This dual lumen device allows contaminated secretions to enter an evacuation port near the top of the balloon cuff of the endotracheal tube. The secretions are removed through the evacuation tube, which is connected to wall suction. However, there are several limitations of this device which can sometimes render it ineffective to treat the problem of subglottic secretion pooling with minimal invasion to the patient. The tube may in some circumstances become plugged frequently, reducing its usefulness to the patient unless he or she is reintubated, which is not desirable since intubation should be performed as infrequently as possible as it is considered to be a high-risk procedure. Also, the outside diameter of the Hi-Lo tube is larger than other tubes on the market of the same internal diameter because of its double lumen, which can cause patient discomfort or stress on the vocal cords which have to be pread wider to accommodate this tube. The bulkiness of the Hi-Lo device presents another obstruction to the ease of intubation, removal, and reintubation.

Additionally, a problem with the existing devices with an integral suction channel is that they can also sometimes become plugged with material, requiring replacement of the endotracheal tube, an undesirable action.

All of the references above are incorporated by reference herein, and the description herein of problems and disadvantages of known apparatuses, methods, and devices is not intended to limit the invention to the exclusion of any aspects of these known entities. Indeed, some embodiments of the invention may include aspects of one or more of the known apparatuses, methods, and devices, while at least to some extent, being free from the disadvantages and problems noted herein.

SUMMARY OF THE INVENTION

The foregoing needs are met, to a great extent, by the present invention, wherein in one aspect is provided in some embodiments a method and device for minimally invasive removal of accumulated subglottic secretions from a ventilator-assisted patient's endotracheal tube.

In accordance with one embodiment of the invention, a tracheal fluid removal device for removing accumulated secretions from an endotracheal tube is provided which can include a dual-track guidance rail having an exterior track and an interior track, a pair of guidance rail connectors connected to the dual-track guidance rail that can be attached to the endotracheal tube, a suction catheter, a retention connector attaching the suction catheter slidably to the endotracheal tube, a slider positioned slidably between the exterior track and interior track, and attached to an end of the suction tube to move the suction tube, and a suction guide attached to the slider for moving the slider along a trajectory between the exterior track and the interior track In accordance with another embodiment of the invention, a tracheal fluid removal device for removing accumulated secretions from an endotracheal tube is provided, which can include a guidance track having an external guide rail and an internal guide rail, wherein each guide rail has an upper and lower end, first and second C-rings having first and second segments, such that the first segment is connected to the guide rails and the second segment is encircled around the endotracheal tube, a suction guide having upper and lower terminal ends and positioned slidably between exterior and interior guide rails, an insertion aid attached to the suction guide, and a suction catheter attached to the suction guide proximate the lower terminal end thereof and positioned alongside the endotracheal tube such that the trajectory of the suction catheter alongside the endotracheal tube corresponds to the movement of the suction guide.

In accordance with another embodiment of the invention, a tracheal fluid removal device for removing accumulated secretions from an endotracheal tube is provided, which can include a suction guide attached to the endotracheal tube and having an opening, a suction guide connector for slidably attaching an upper end of the suction guide to the endotracheal tube, at least one retention ring located above a lower end of the endotracheal tube; and a suction catheter, wherein the retention ring slidably connects a lower end of the suction guide to the endotracheal tube, and further wherein the suction catheter is inserted into the opening of the suction guide and passed toward said lower end to remove accumulated subglottic secretions.

In accordance with yet another embodiment of the invention, a tracheal fluid removal device for removing accumulated secretions from an endotracheal tube is provided, which can include guiding means connected to the endotracheal tube, a suction catheter, means for slidably mounting the suction catheter to the endotracheal tube, and engaging means attached to the suction catheter for slidably engaging the guiding means to guide the suction catheter towards a lower end of the endotracheal tube.

In accordance with still another embodiment of the invention, a tracheal fluid removal device for removing accumulated secretions from an endotracheal tube is provided, which can include engaging means having upper and lower terminal ends, guiding means for guiding the engaging means towards a lower end of the endotracheal tube, and a suction catheter attached to the guiding means and positioned alongside the endotracheal tube such that the trajectory of the suction catheter alongside the endotracheal tube corresponds to the movement of the guiding means along the guiding means.

In accordance with yet another embodiment of the invention, a tracheal fluid removal device for removing accumulated secretions from an endotracheal tube is provided, which can include guiding means attached to the endotracheal tube and having an opening, means for attaching the guiding means to the endotracheal tube, and a suction catheter, wherein the suction catheter is inserted into and through the opening of the guiding means and passed toward said lower end to remove accumulated subglottic secretions.

In accordance with still another embodiment of the invention, a method for removing accumulated secretions from an endotracheal tube includes guiding a suction catheter along a path adjacent the endotracheal tube using a guidance rail attached to the endotracheal tube and a suction guide attached to the suction catheter by sliding the suction guide along the rail, and positioning an end of the suction catheter near a lower end of the endotracheal tube.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
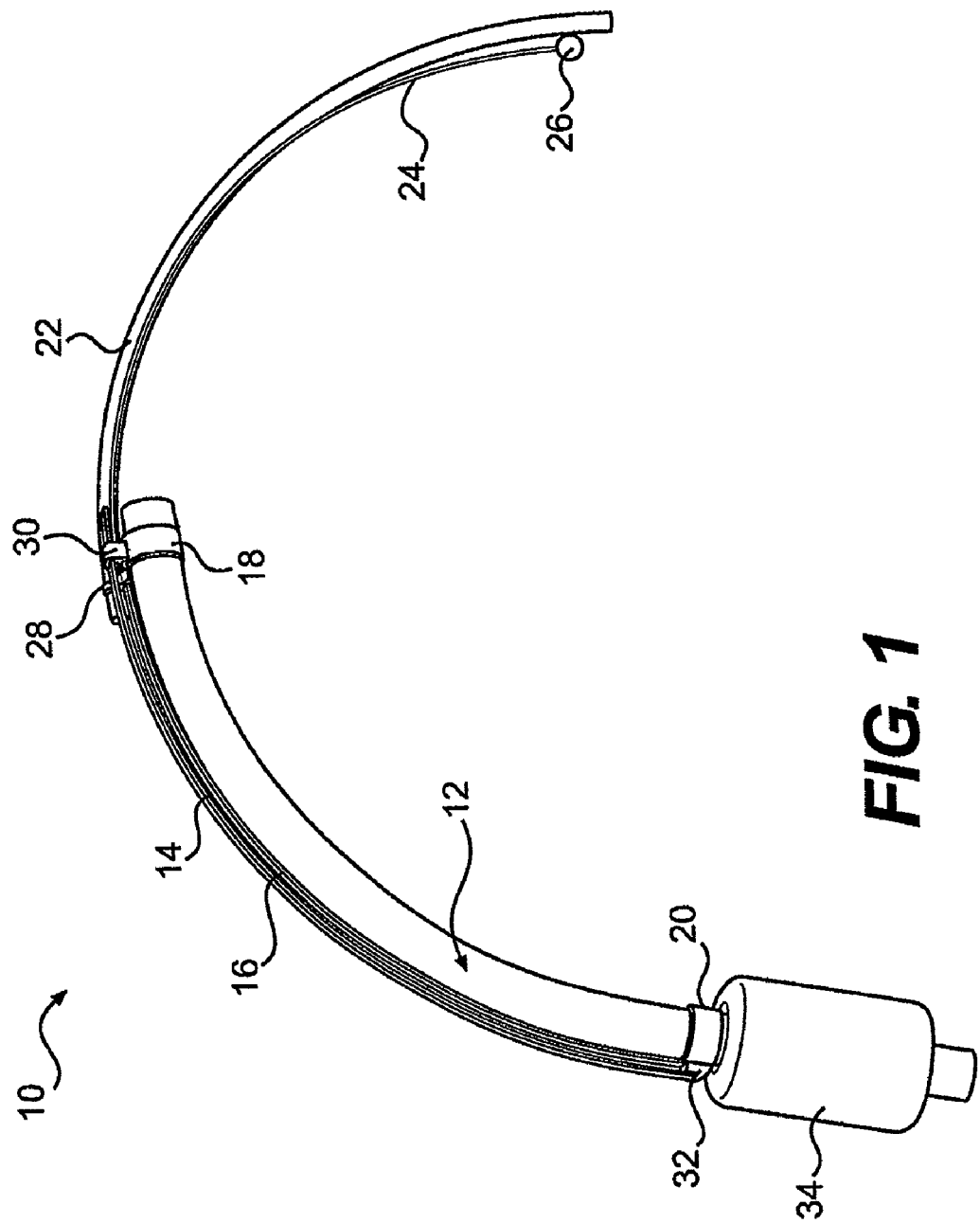
FIG. 1 is a perspective view illustrating an exemplary component assembly of a tracheal fluid removal system according to a preferred embodiment of the invention.

Some embodiments of the present invention relate to a guide rail attached to an endotracheal tube that enables a suction catheter to be guided into a patient's oropharynx and upper trachea above the endotracheal tube cuff for the removal of fluids and secretions that collect there. Some embodiments also may be used as a first component in the treatment of VAP wherein a second component pertains to the use and delivery of nitric oxide gas to the trachea and oropharyngeal area of an intubated patient to decontaminate the area and kill or inhibit the growth of microorganisms that may grown in this area. Some preferred embodiments of the invention will now be described with reference to the drawing figures, in which like reference numerals refer to like parts throughout.

An embodiment of the present inventive apparatus and method is illustrated in FIGS. 1-7. With reference to FIG. 1, an assembled tracheal fluid suction device 10 is shown with a dual-rail suction guide mounted to a patient's endotracheal tube 12 by a pair of C-shaped rings 18 and 20. One C-ring 20 is located at the distal end of the endotracheal tube 12, directly above the endotracheal tube cuff 34. The second C-ring 18 is located at the proximal end of endotracheal tube 12, near the juncture where the endotracheal tube 12 exits the patient's mouth. C-rings of varying sizes may prefabricated to fit different sized endotracheal tubes, since different manufacturers make endotracheal tubes of varying diameters. Accordingly, it will be appreciated that some embodiments provide a method and device for the attachment, removal, and operative guidance of replaceable suction catheters, with a variety of adapters customizable to fit various sized endotracheal tubes.

In some embodiments, the tracheal fluid removal device has a guide of a small width so as to minimize patient discomfort during device use. The dual-rail suction guide includes an exterior rail 14 and an interior rail 16 having lengths generally commensurate with the patient's endotracheal tube 12. The exterior rail 14 protects the larynx from the sliding movement of the suction catheter (further described below) and its positioning mechanism (also further described below). The interior rail 16 consists of an I-beam or T-beam design. Each rail has an upper end and a lower end, to which receiving caps 30 and 32 are affixed. The receiving caps 30 and 32 are also affixed to C-rings 18 and 20. The receiving cap 30 has two apertures to contain the upper ends of the exterior rail 14 and interior rail 16, respectively. As illustrated in FIG. 1, the top aperture of the receiving cap 30 accepts the upper end of exterior rail 14, which passes through and extends towards the end of endotracheal tube 12. The bottom aperture accepts the upper end of lower rail 16 and caps the end of the rail 16 therein.

Correspondingly, just above the endotracheal tube cuff 34 is the receiving cap 32, having two apertures to receive the lower ends of the exterior rail 14 and interior rail 16. (In the embodiment shown in FIG. 6, both apertures enclose the ends of the rails such that there is no pass-through feature to allow the rail ends to extend beyond the cap 32.) Offset to the side of the endotracheal tube 12 is a suction catheter 22, which is held in position by a suction catheter retention connector 28, which can be a C-shaped ring or any other design that can hold a suction catheter 22. The suction catheter 22 may have characteristics such as ridges that will provide some frictional holding force against the retention connector 28. The suction catheter 22 can selectively be advanced from a retracted position with its end near the patient's airway opening to an extended position with its end abutting or nearly abutting the endotracheal tube cuff 34 so that the fluid and material above the cuff 34 can be removed. The suction catheter 22 is passed on the outside of the tube 12 through the vocal cords on the longer dimension of the triangular-shaped vocal cords. Therefore, the suction catheter 22 does not put additional lateral pressure on the shorter dimensions where the actual cords are located. If the suction catheter 22 becomes plugged, it can be retrieved and cleaned, or replaced and repositioned.

In this preferred embodiment, the suction catheter retention connector 28 is a C-shaped ring. The retention connector 28 also forms a slider cap 36 that slides between the exterior rail 14 and the interior rail 16 with a trajectory that extends generally on a path of travel from receiving cap 30 to receiving cap 32. The slider cap 36 is attached to a suction guide 24, which is a wire that is held and manipulated by the intubating medical professional for easy insertion and retrieval of the suction catheter 22. The suction guide 24 is also positioned in between the exterior rail 14 and the interior rail 16, which moves simultaneously with the movement of the suction catheter 22 during adjustment as it travels down the length of the patient's endotracheal tube 12. A retrieval ball 26 is attached to the end of the suction guide 24, and serves as a handle for the medical professional.

Figure 2:
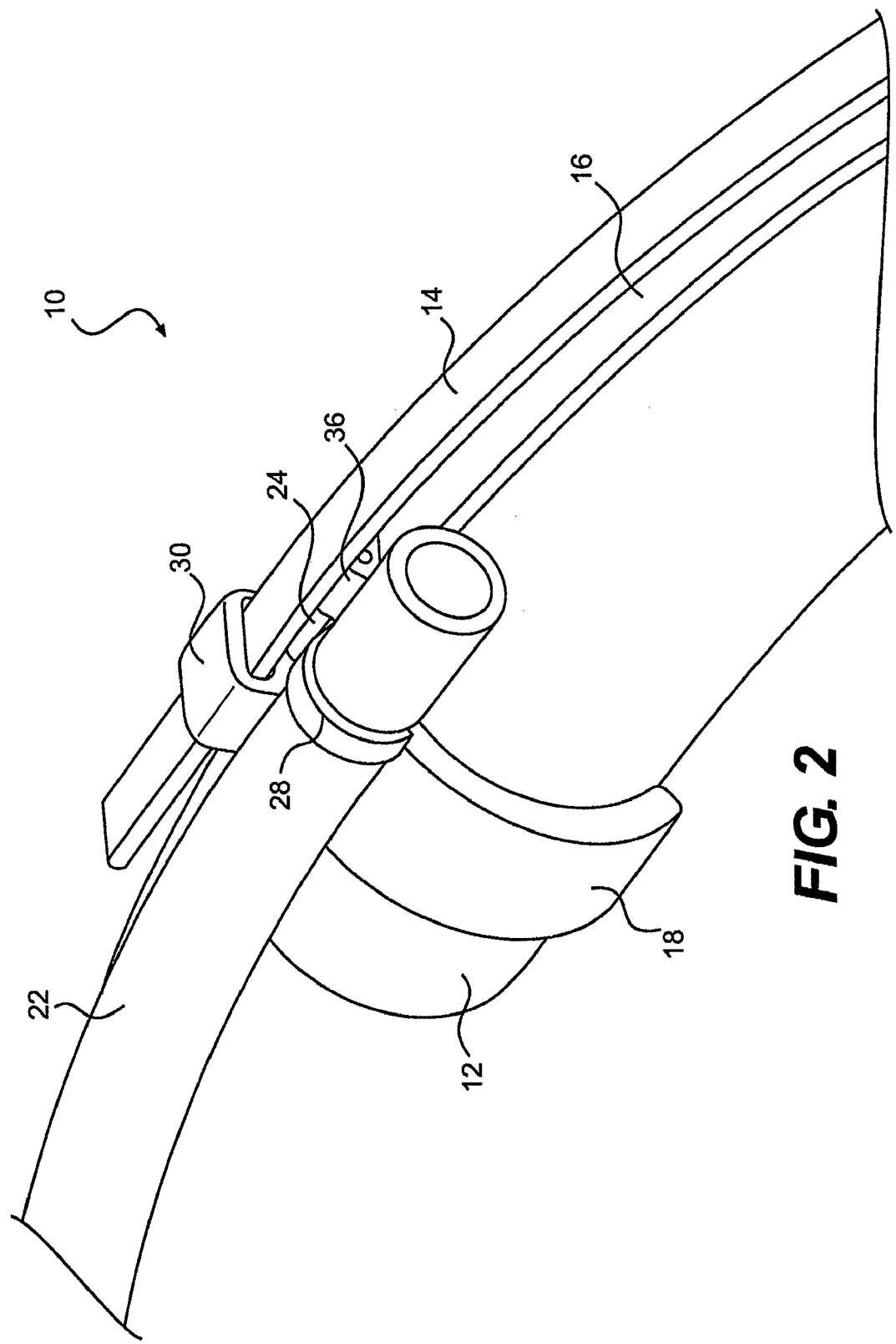
FIG. 2 is an enlarged top view of an upper segment of the assembly of FIG. 1.

FIG. 2 is an enlarged view of the proximal end of the endotracheal tube 12, wherein the components of the upper assembly of a preferred embodiment of the apparatus of the present invention are presented in detail. This figure provides a view of the offset positioning of the suction catheter 22 relative to the endotracheal tube 12 and the interacting attachment components. The ring of the C-shaped retention connector 28 encircles the suction catheter 22 and converges to form the slider cap 36, which is attached to the end of the suction guide 24. FIG. 2 shows the suction guide 24 extending through the receiving cap 30 and into the slider cap 36. An interior wall of the slider cap 36 has an aperture or receiving end that encases the end of suction guide 24. The slider cap 36 slides on top of the interior rail 16 and underneath the exterior rail 14 as the suction guide 24 is inserted into and retrieved from the patient's trachea.

Figure 3:
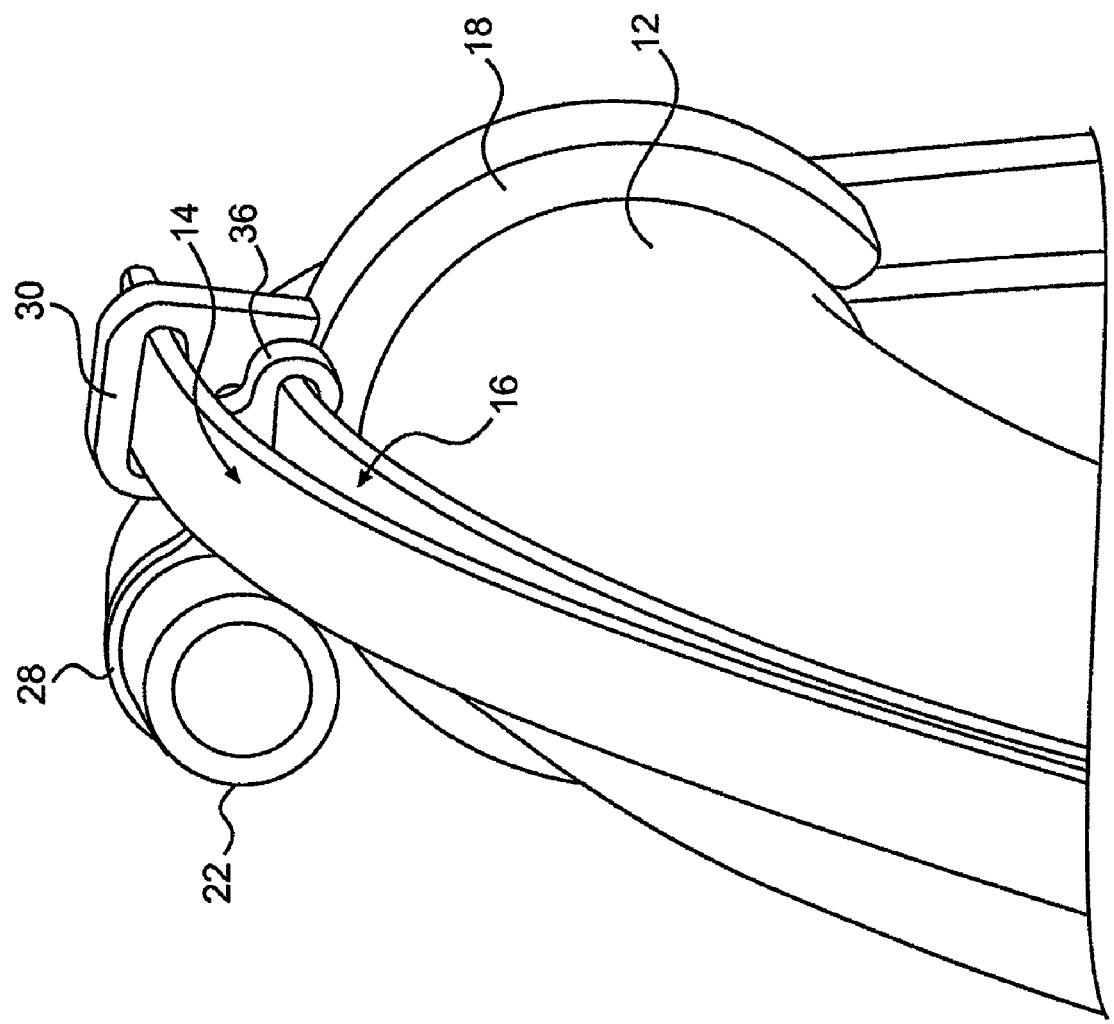
FIG. 3 is an enlarged rear view of the upper segment illustrated in FIG. 2.
Figure 4:
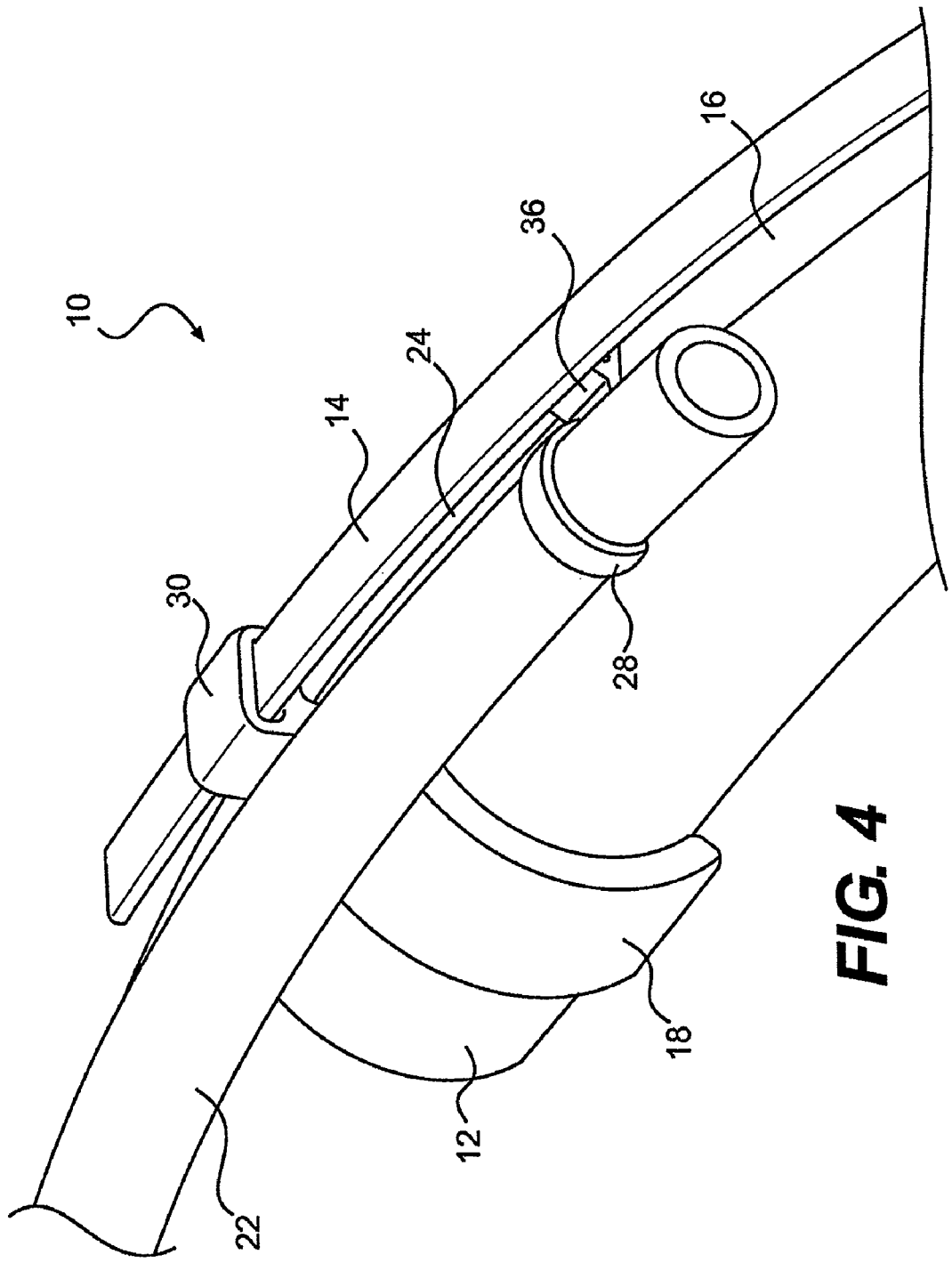
FIG. 4 is side view of the exemplary assembly of FIG. 1 illustrating the directional movement of the exterior tube and corresponding interior guide rail adjustment.

FIG. 3 is an enlarged frontal view of the guide rail assembly. In a preferred embodiment, the slider cap 36 has a lower aperture which the interior rail 16 extends therethrough, thus allowing the slider cap 36 to slide on top of the interior rail 16 and remain in an upright position as it moves along its trajectory down the rail and alongside endotracheal tube 12. The movement of the slider cap 36 and the attached suction guide 24 is illustrated in FIG. 4. The suction guide 24 traverses through the aperture in the receiving cap 30 as it is inserted down the patient's trachea. The attached suction catheter 22 is illustrated as its position shifts with the movement of the suction guide 24.

Figure 5:
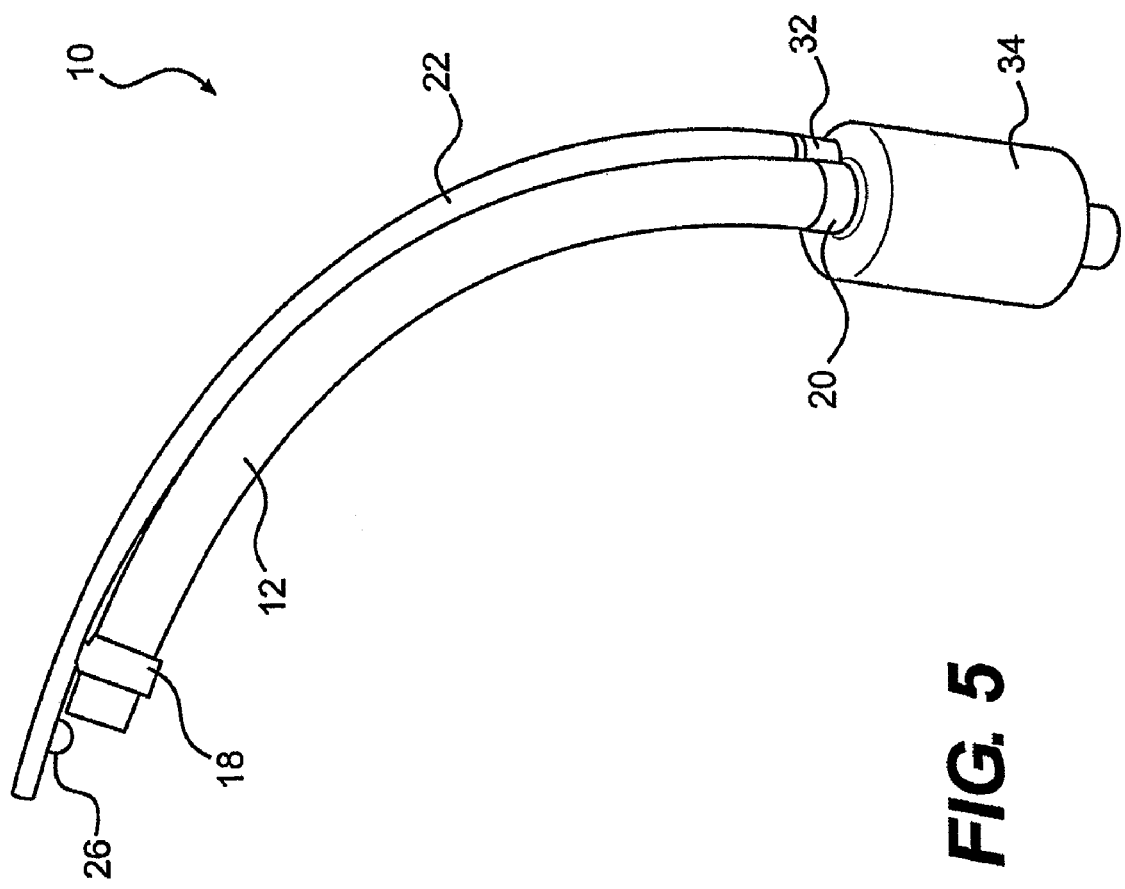
FIG. 5 is a perspective view showing the positioning of the exterior suction tube of FIG. 1 after completion of its route alongside the patient's endotracheal tube.
Figure 6:
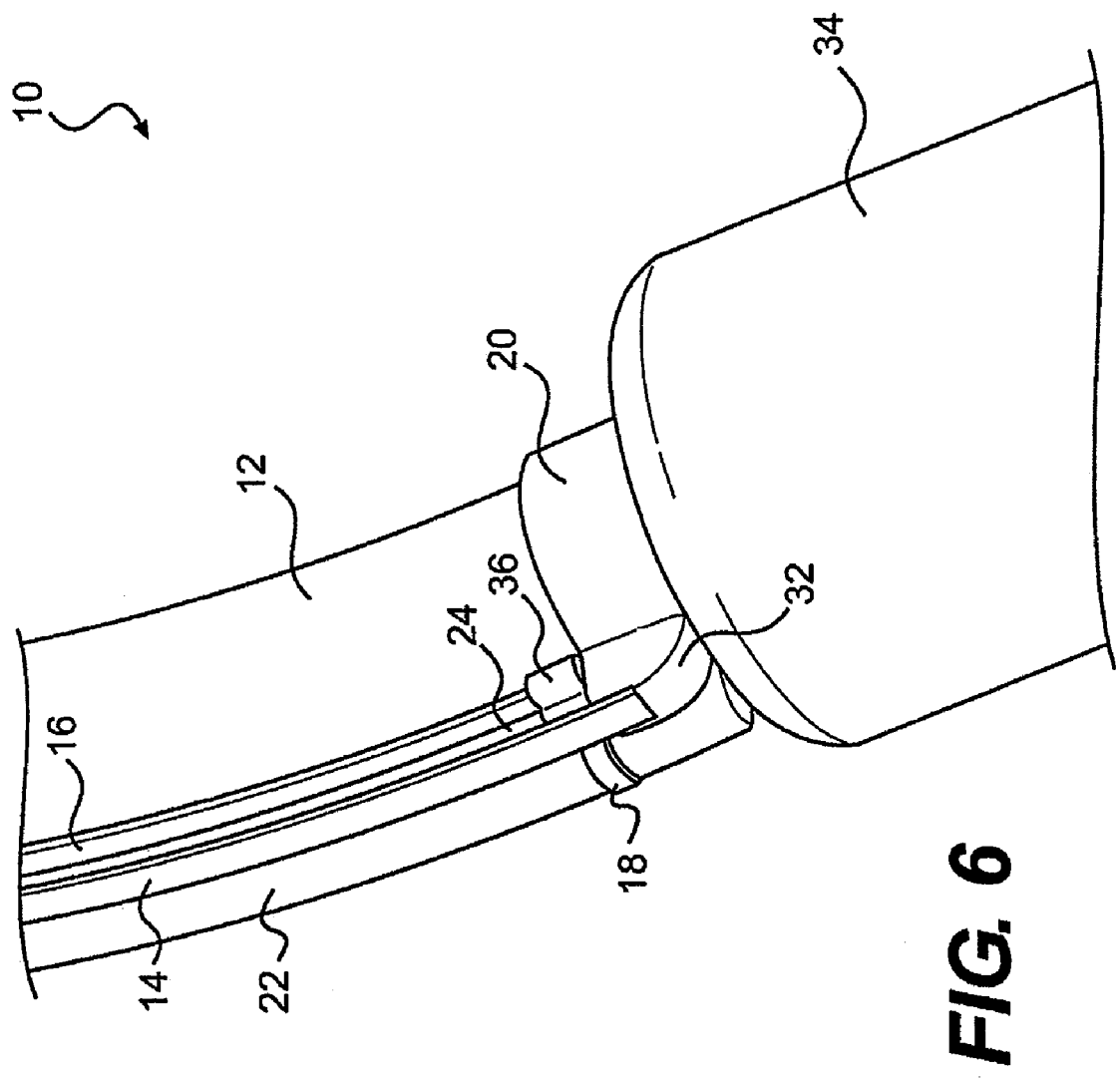
FIG. 6 is an enlarged rear view of a lower segment of the assembly illustrating the positioning depicted in FIG. 5.

When the trajectory of the suction guide 24 and suction catheter 22 is complete, the apparatus is configured in the position shown in FIG. 5. The suction catheter 22 abuts or nearly abuts the endotracheal tube cuff 34 such that a substantial portion of the length of the catheter 22 spans along the length of endotracheal tube 12. The retrieval ball 26 is located just above the endotracheal tube 12 allowing for easy retraction of the ball 26 and the attached guide 24. FIG. 6 is a frontal view of the lower segment of the device just above the endotracheal tube cuff 34. The top of the receiving cap 32 holds the lower end of the exterior guide rail 14. The slider cap 36 lies adjacent to the receiving cap 32 and the C-ring 20. The suction guide 24 has moved down the length of the interior rail 16.

Figure 7:
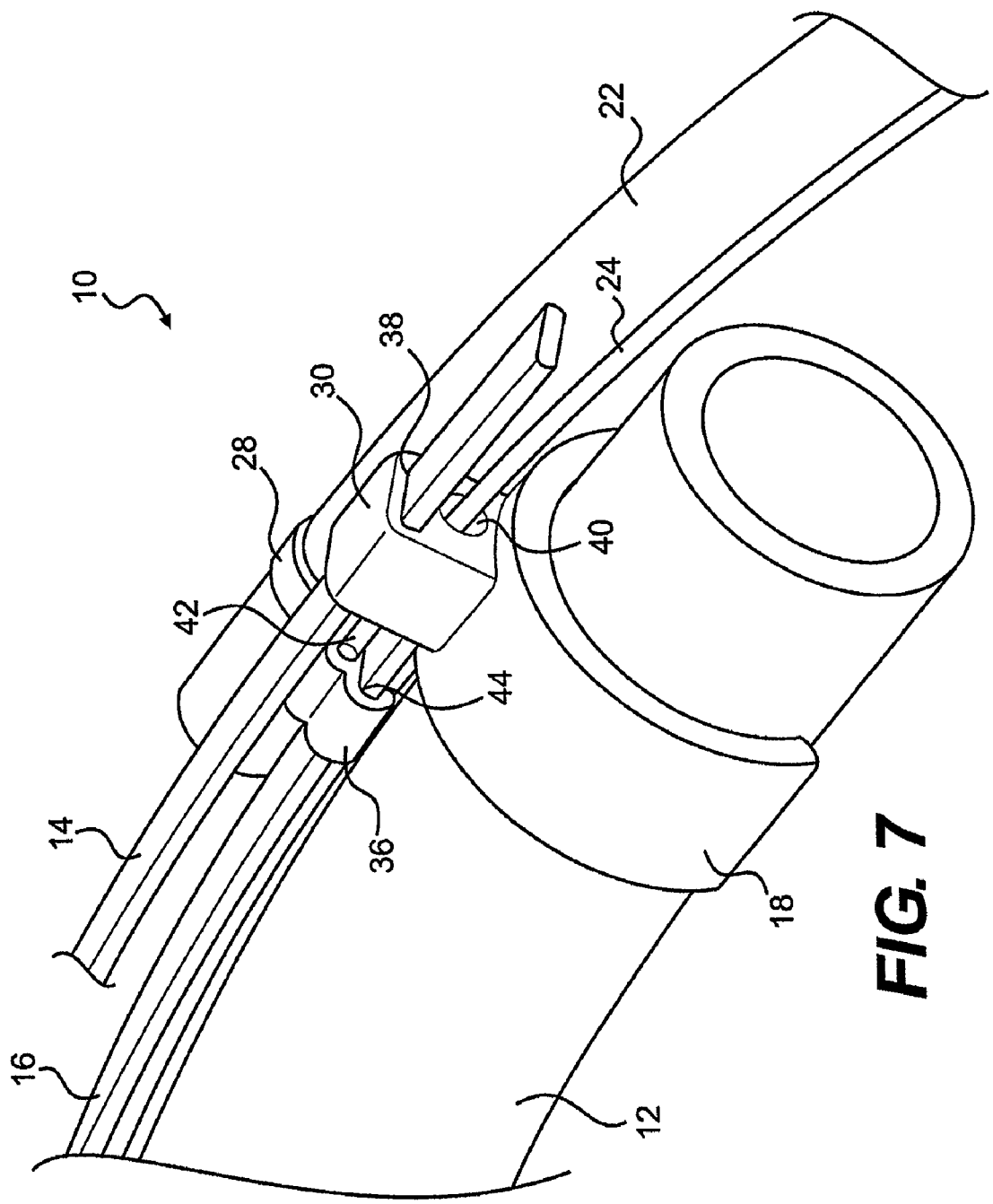
FIG. 7 is an enlarged top view of an upper segment of the assembly of FIG. 1, depicting the positioning of the components after a completed retraction of the exterior suction tube.

After the medical professional retracts the suction guide 24 to remove and clean the suction catheter 22, the suction guide 24 is moved to a fully retracted position, as shown in FIG. 7. FIG. 7 also shows the apertures in the receiving cap 30 and slider cap 36. The exterior rail 14 extends through the receiving cap 30 via aperture 38, which is shaped to fit the corresponding shape of the extension rail 14. The suction guide 24 is retracted through the circular aperture 40 in the receiving cap 30. The top of the slider cap 36 has an aperture 42 for receiving the guide tube 24 into the interior wall of the slider cap 36. The pass-through aperture 44 of the lower portion of the slider cap 36 is fitted to allow passage of the interior rail 16 therethrough.

Figure 8:
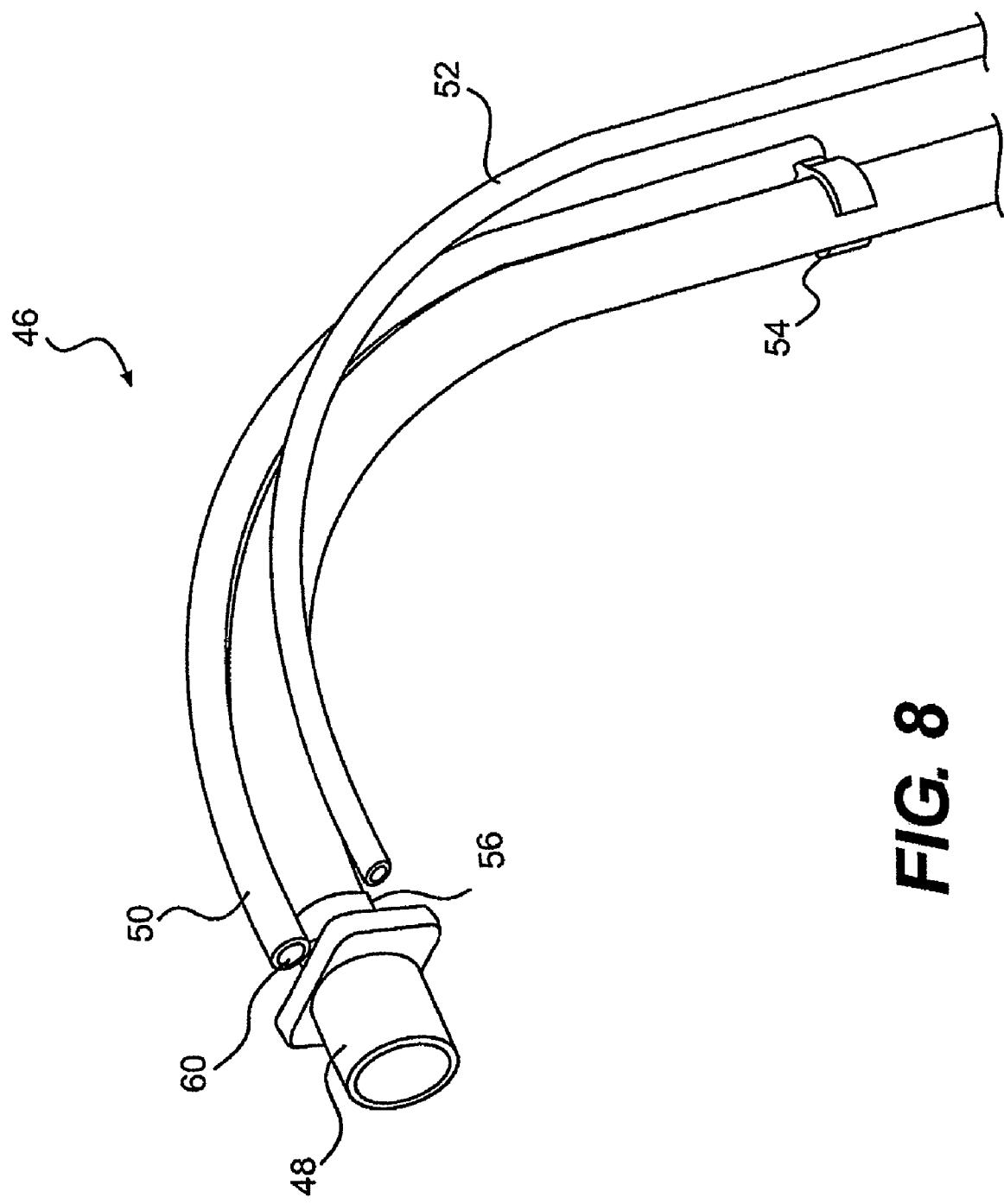
FIG. 8 is a perspective view illustrating components of a tracheal fluid removal system according to an alternative embodiment of the invention.
Figure 9:
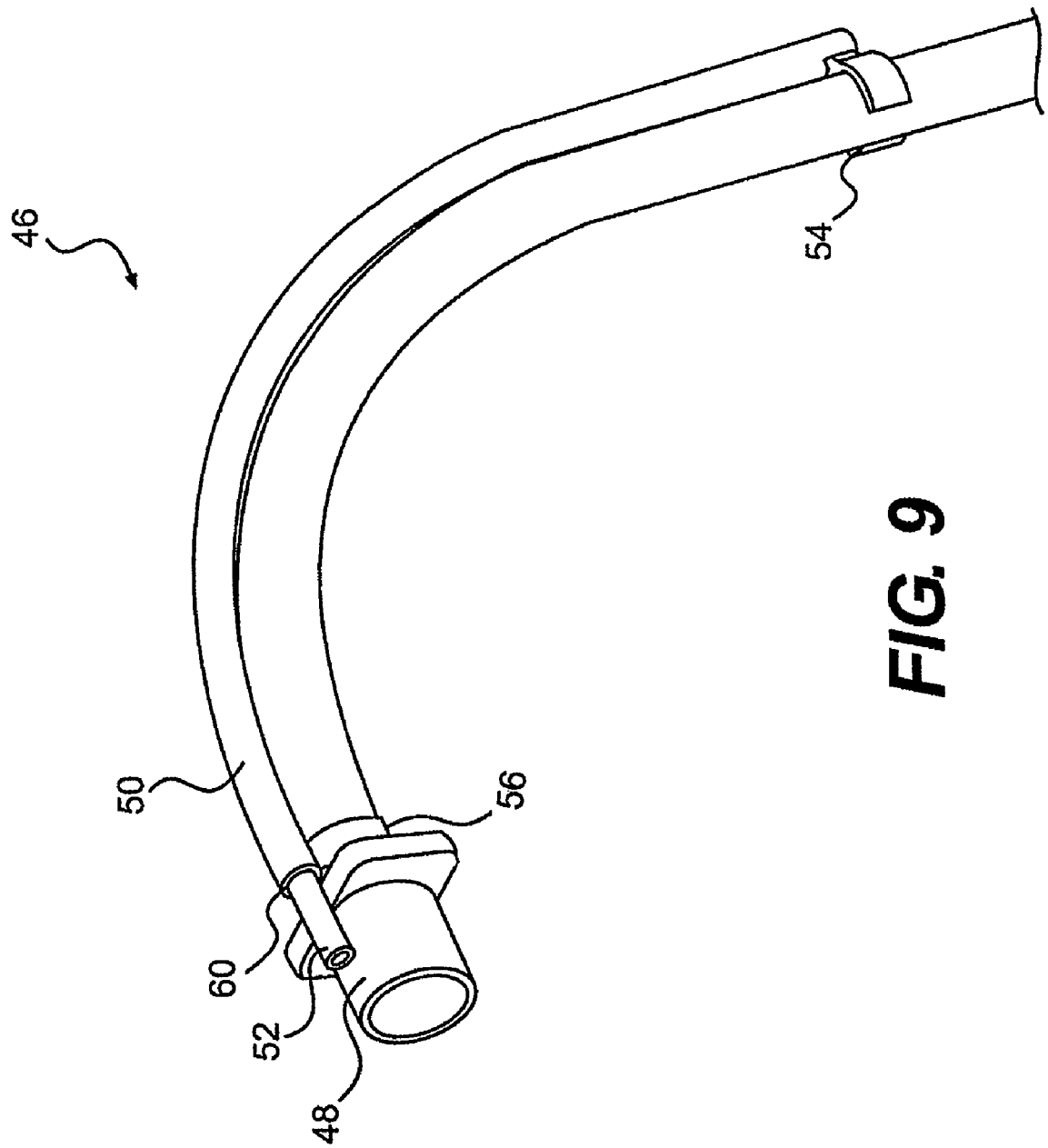
FIG. 9 is a perspective view of an assembled tracheal fluid removal system according to the embodiment of FIG. 8.

An alternative embodiment of the tracheal fluid removal apparatus is illustrated in FIGS. 8 and 9. FIG. 8 shows a tracheal fluid removal apparatus 46 comprising a tube-like suction guide 50 bonded to a C-ring on an endotracheal tube 48. The suction guide 50 may be fixably attached to the C-ring by other means well known in the art. At the upper end of the tube 48, just above the C-ring is the guide stop 56. At the upper end of the suction guide 50 is suction guide opening 60. The lower end of the suction guide 50 is removably attached to the endotracheal tube 48 by left and right clips 54. An endotracheal tube cuff (not shown) encapsulates the lower end of the endotracheal tube 48, as shown in the preferred embodiment described above.

The suction tube 52 is depicted alongside the apparatus in FIG. 8. FIG. 9 shows the completed assembly as the suction tube 52 is inserted into the suction guide 50 by way of the suction guide opening 60. In accordance with this alternative embodiment of the present invention, the suction tube 52 may be removed for cleaning or replacement without invasive physical maneuvering or surgical means.

Although the examples of the device are described and depicted utilizing a circular suction catheter and guide, it will be appreciated that other catheter and guide designs having various geometries can be used. Moreover, while the embodiments of the invention are depicted and described in conjunction with a balloon cuff, the various embodiments of the present invention may be utilized without a balloon cuff and such a cuff is not required for utilization of the invention. Also, although the device is useful to treat human patients in a hospital, it can also be used on other intubated mammals in various settings.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A tracheal fluid removal device for removing accumulated secretions from an endotracheal tube, comprising:
   a dual-track guidance rail having an exterior track and an interior track;
   a pair of guidance rail connectors connected to the dual-track guidance rail and attached to the endotracheal tube;
   a suction catheter;
   a retention connector attaching the suction catheter slidably to the endotracheal tube;
   a slider positioned slidably between the exterior track and interior track, and attached to an end of the suction catheter to move the suction catheter; and
   a suction guide attached to the slider for moving the slider along a trajectory between the exterior track and the interior track.

2. The tracheal fluid removal device of claim 1, wherein the guidance rail connectors each comprise a C-ring.

3. The tracheal fluid removal device of claim 2, wherein the C-rings are pre-sized to fit a variety of endotracheal tube diameters.

4. The tracheal fluid removal device of claim 1, wherein an insertion aid is attached to an upper terminal end of the suction guide.

5. The tracheal fluid removal device of claim 4, wherein the insertion aid is a wire.

6. The tracheal fluid removal device of claim 1, wherein the guidance rail connectors each have a plurality of apertures for receiving upper and lower terminal ends of the exterior and interior tracks.

7. The tracheal fluid removal device of claim 6, wherein the guidance rail connectors are a first guidance rail connector and a second guidance rail connector.

8. The tracheal fluid removal device of claim 7, wherein the first guidance rail connector has an aperture for receiving the suction guide such that the suction guide passes inside the aperture on its trajectory atop the second guidance rail.

9. A tracheal fluid removal device for removing accumulated secretions from an endotracheal tube, comprising:
   a guidance track having an external guide rail and an internal guide rail, wherein each guide rail has an upper and lower end;
   first and second C-rings having first and second segments, such that the first segment is connected to the guide rails and the second segment is encircled around the endotracheal tube;
   a suction guide having upper and lower terminal ends and positioned slidably between exterior and interior guide rails;
   an insertion aid attached to the suction guide, wherein said insertion aid is a wire; and
   a suction catheter attached to the suction guide proximate the lower terminal end thereof and positioned alongside the endotracheal tube such that a trajectory of the suction catheter alongside the endotracheal tube corresponds to movement of the suction guide.

10. The tracheal fluid removal device of claim 9, wherein the first and second C-rings attach to the endotracheal tube at upper and lower ends of said guide rails, respectively.

11. The tracheal fluid removal device of claim 9, wherein the lower terminal end of the suction guide comprises a slider that connects the suction guide to the suction catheter and wherein the slider is slidable along the guidance rail.

12. The tracheal fluid removal device of claim 11, wherein the slider comprises a C-ring suction catheter retention connector.

13. A method for removing accumulated secretions from an endotracheal tube, comprising:
   guiding a suction catheter along a path adjacent the endotracheal tube using a guidance rail attached to the endotracheal tube and a suction guide attached to the suction catheter by sliding the suction guide along the rail in response to manipulation of an insertion aid wire coupled with the suction guide; and
   positioning an end of the suction catheter near a lower end of the endotracheal tube.

14. The method of claim 13, further comprising moving the suction catheter along the path using part of the suction guide as a handle.

* * * * *